(12) United States Patent
Colitz et al.

(10) Patent No.: US 8,709,515 B1
(45) Date of Patent: Apr. 29, 2014

(54) NUTRITIONAL SUPPLEMENT METHOD

(76) Inventors: Carmen C. H. Colitz, Jupiter, FL (US);
Terri L. McCalla, Bellingham, WA (US); Debra A. Smith, Seattle, WA (US)

( * ) Notice: Subject to any disclaimer, the term of this patent is extended or adjusted under 35 U.S.C. 154(b) by 63 days.

(21) Appl. No.: 13/428,341

(22) Filed: Mar. 23, 2012

Related U.S. Application Data

(63) Continuation-in-part of application No. 12/378,738, filed on Feb. 19, 2009, now abandoned.

(51) Int. Cl.
*A61K 36/87* (2006.01)
*A61K 36/45* (2006.01)
*A61K 36/16* (2006.01)
*A61K 31/385* (2006.01)

(52) U.S. Cl.
USPC ........... 424/766; 424/732; 424/752; 514/440; 514/912; 514/913

(58) Field of Classification Search
None
See application file for complete search history.

(56) References Cited

U.S. PATENT DOCUMENTS 6,649,195 B1 * 11/2003 Gorsek .......................... 424/732

OTHER PUBLICATIONS

Mares-Perlman, et al. (2002) J. Nutr. 132: 518S-524S.*
Barden et al. (2008) AJVR, vol. 69, No. 1, 94-100.*
Fullmer et al. (2001) Cereal Foods World vol. 46, No. 9, 408-413.*

* cited by examiner

*Primary Examiner* — Chris R Tate
*Assistant Examiner* — Russell Fiebig

(57) ABSTRACT

The method comprises steps of: providing a nutraceutical including, in combination, 1.13 to 3 mg lutein and 18.8 to 51.2 mg omega fatty acids and 1.9 to 5.2 mg grape seed extract and 1.9 to 5.2 mg alpha lipoic acid; determining the weight of each dose of the components in the combination based upon an amount per kg body weight of the animal patients; and administering 1 dose of nutraceutical per day to animals suffering from ocular health issues including any degenerative retinal disease and diabetic cataracts and prior to and following cataract surgery for the diminishment and prevention of secondary cataracts.

3 Claims, No Drawings

NUTRITIONAL SUPPLEMENT METHOD

RELATED APPLICATION

The present application is a continuation-in-part of pending application Ser. No. 12/378,738 filed Feb. 19, 2009, the subject matter of which is incorporated herein by reference.

FIELD OF INVENTION

The invention is directed to maintain ocular health, slow the progression of inherited and age related retinal degeneration, possibly slow or halt the death of photoreceptors in Sudden Acquired Retinal Degeneration Syndrome, SARDS; provide mild anti-inflammatory benefits (lutein, GSE, others); possibly slow or prevent the cataractous changes due to retinal degeneration and senile changes and chronic sunlight exposure; and possibly benefit diabetic patients as many components help to stabilize glucose use and metabolism. The invention has been shown to significantly slow the onset of diabetic cataracts. A research project is presently ongoing.

BACKGROUND OF THE INVENTION

The Lens—The crystallin lens is a transparent biconvex, M&M shaped, structure located behind the iris of the eye. The basic anatomy of the lens includes an outer lining, lens capsule, surrounding the lens material. The lens material has two major subdivisions, the nucleus, which is the innermost aspect, and the surrounding layers, called the cortex. The anterior aspect of the lens capsule is lined with a single layer of cells called the lens epithelial cells. There are three distinct subgroups of these cells: the central region has cells that are very slow to proliferate unless they undergo trauma, such as cataract surgery, the germinative region has cells that are proliferative and their progeny migrate laterally to the equatorial region. The cells in the equatorial region develop into elongated fiber cells that span from the anterior aspect to the posterior aspect of the lens, with the newer cells overlying the older cells in an organized pattern, similar to rings in a tree trunk. The lens' function, along with the cornea, is to focus light onto the retina for sight. In humans, non-human primates, and some other species the lens can change shape in order to continually focus on objects located at different distances. This change in shape is called accommodation and is strongest in youth, but becomes more difficult with normal aging as the lens becomes more densely packed with cells.

The internal portion of the eye has two fluid-containing chambers: the anterior segment contains the aqueous humor or aqueous, and the posterior segment contain the vitreous humor or vitreous. Both of these fluids bathe the lens and provide nutrients and take away waste material.

Cataracts—A cataract is any opacity of the lens capsule or its cortex or nucleus or any combination of these and can affect all species of animals. Causes of cataracts are numerous and include excessive exposure to oxidative stressors, including ultraviolet irradiation or sunlight, as well as other forms of radiation, genetics, diabetes mellitus, nutritional imbalance, toxins, and normal aging changes, among others. Thus far, there is no medical way in which to treat an existing cataract, only surgery to remove the cataract will address the problem. The incidence of cataracts in the general animal and human population depends on the definition. If defined as just any opacity that affects the lens or its capsule, then the incidence is likely very high. However, if this opacity significantly impacts vision, then the incidence may only affect less than five percent of all animals. This percentage increases with age in all species. It is estimated that 10,000 to 12,000 cataract surgeries are performed annually in dogs; this makes it one of the most common surgical procedures performed in this species. Cataract surgery is also the most common surgery performed in humans.

There are species differences in terms of causes of cataracts. The leading cause of cataracts in humans is exposure to sunlight; other causes include diabetes mellitus and inheritance. Common causes of cataracts in dogs are inheritance, breed-predisposition, and diabetes mellitus. Cats develop visually impairing cataracts due to chronic uveitis as do horses; though both species can uncommonly develop inherited or nutritional cataracts.

Retina—Retinal Degeneration aka Progressive Retinal Atrophy is another inherited disease that affects dogs more commonly than cats or other species. Numerous pure breed dogs and a few pure breed cats have been shown to be genetically predisposed to this problem. The disease is typically diagnosed by ophthalmoscopy when the dogs are young adults, under 6 years of age; though some forms of the disease can begin earlier. However, the disease can be diagnosed in most forms before 1.5 years of age by electroretinography. The majority of inherited retinal degenerations affect the rods first, then eventually the cones; very few affect the cones first.

Sudden Acquired Retinal Degeneration Syndrome (SARDS) is another type of retinal degeneration with an unknown cause that affects the rods and cones acutely. It typically affects middle-aged spayed female dogs, though any breed or sex can be affected. Dogs present with a sudden loss of vision over a few days to 1-2 weeks. The pupils usually respond to light incompletely until late in the disease. Early, there are negligible fundic changes, however, with time, the arterioles attenuate more rapidly than the venules. Histologically, the rods and cones die by apoptosis, which explains the electroretinographic results ie flat with no wave form. Over time, the rest of the retinal layers degenerate. To date, there is no way to cure this disease once vision is completely lost.

Dietary Supplements are commonly used for the prevention of chronic disease, improved overall health, and in some cases to treat or address some medical conditions. Their use for specific ocular conditions has been advocated in the literature; these include retinal or macular degeneration, cataracts, dry eye and others.

Recent literature suggests that glucose, fatty acids, amino acids, vitamins, minerals, supplements, other nutrients or their respective metabolites regulate gene expression in a hormone-independent manner. In fact, bioactive food components, including vitamins, minerals, carotenoids, flavonoids, monoterpenes and phenolic acids are now thought to act as transcriptional modulators directly affecting gene expression. Obesity is a risk factor for cataract formation in humans. Therefore, perhaps improving the overall health status of the human or animal but supplementing with antioxidants may modulate genes that predispose that human or animal to genetic or environmentally induced diseases.

Carotenoids—Epidemiological and interventional studies suggest that increased consumption of foods rich in antioxidants such as vitamin C, vitamin E and selective carotenoids protect the human and primate lens against UVR-induced oxidative stress and thereby decrease the risk of developing cataracts. Recent attention has focused on the possible roles of lutein, LUT; and zeaxanthin, ZEA, in ocular health. These oxycarotenoids, oxygenated carotenoids or xanthophylls, selectively accumulate in the lens and the macular region of the human and primate accumulate in the lens by unknown mechanisms. There are also trace levels of lutein and zeaxanthin in the cornea and sclera, the lens and uveal structures have higher levels. The macula has 33 ng and the peripheral retina has 65 ng of these carotenoids. It has been proposed that these compounds may be particularly effective in preventing cataracts and age-related macular degeneration. Indeed, increased plasma and/or dietary levels of these carotenoids are associated with significantly decreased risk of developing cataracts and macular degeneration. Conversely, experimental animals, e.g., primates, fed diets lacking LUT and ZEA are significantly more susceptible to developing cataracts. One human study found that lutein and zeaxanthin appears beneficial for age-related macular degeneration and cataract formation. Such observations have resulted in the appearance of numerous lutein supplements in the human health marketplace. For example, Centrum multi-vitamin and mineral pills now include lutein and the label indicates that this carotenoid "helps maintain healthy eyes".

The importance of dietary LUT and ZEA in canine vision and cataractogenesis is unknown. Kim et al. recently reported that LUT was not detectable in the plasma of 18 month old beagles fed a standard canine diet. However, plasma LUT increased rapidly and immune function was enhanced in response to dietary supplementation with LUT. The possibility that LUT supplementation resulted in the accumulation of the xanthophylls in ocular tissues was not examined. Since supplementation of humans and primates with xanthophylls induced a gradual increase in retinal xanthophylls in humans and primates, 10, 11 it is feasible that LUT and ZEA will accumulate in canine ocular tissues in response to supplementation.

Lycopene is another major carotenoid which is found primarily in tomatoes. Of all known carotenoids, lycopene has been shown to have the highest physical quenching rate constant with singlet oxygen species. Lycopene has been shown to protect against cataract formation in vitro and in vivo.

Omega Fatty Acids—Puppies fed diets with high fish oil supplementation had improved visual performance as evidenced by increased rod response using electroretinography. They also had shorter response times, improved response to dim light and increased activation of the neural cascade. Puppies fed either flaxseed oil or only ALA, alpha linoleic acid, the precursor to EPA and subsequently DHA, had lower or minimal improvements in these parameters. This is likely due to the slow and inefficient conversion of ALA to EPA, and then to DHA. Therefore, feeding preformed dietary n-3 long chain PUFAs, polyunsaturated fatty acids, is a more efficient way to enrich diets with DHA. A review of the human literature which evaluated the evidence for the effectiveness of omega-3 fatty acids in preventing the development or progression of retinitis pigmentosa, a disease analogous to Progressive Retinal Atrophy in dogs, found trends in improvement in some of the studies. The same group evaluated the literature for the effectiveness of omega-3 fatty acid in slowing the progression of age-related macular degeneration. Only one study was found, but it demonstrated the efficacy of omega-3 fatty acids in preventing AMD to its advanced form. Omega-3 fatty acids may protect the vascular and neural retina against inflammatory-, light-, ischemia-, oxygen-, and age-related pathology. Omega-3 fatty acids have also been shown to be beneficial for the prevention of cataract in humans.

Vitamin C, Ascorbic Acid—Vitamin C is a hydrophilic molecule that scavenges free radicals. It is the strongest physiological antioxidant that acts in the aqueous environment of the host. It is a very safe antioxidant, likely due to its water solubility, with no safe upper dose limit set by the Expert Group on Vitamins and Minerals of 2003. Vitamin C is found in the lens and in the aqueous humor of most species, including dogs, cats, humans, and cattle. Its function relates to the oxidation-reduction reactions or is coupled to glutathione metabolism. One ten year study found that vitamin C protects against nuclear cataract formation in humans. Numerous other studies found that supplementation with vitamin C and elevated blood levels of this antioxidant were associated with decreased incidence in at least one type of cataract. In humans, vitamin C concentrations decrease with age and more so in patients with senile cataract. A study in Cocker Spaniels found that those with cataracts had lower vitamin C levels than those without cataracts suggesting that there is a decrease in antioxidant capacity in the aqueous humor of dogs with cataracts. Whether this was a cause or an effect was not identified.

Vitamin E—Vitamin E is a fat soluble, lipophilic, antioxidant that interferes with the chain reaction of lipid peroxidation. Vitamin C works synergistically with vitamin E, i.e. vitamin E is oxidized to tocopheroxyl radical which is reduced back to tocopherol by vitamin C. Numerous studies have strongly suggested that consistent intake of vitamin E and high plasma vitamin E levels had a lower prevalence of various types of cataracts in humans. Higher blood levels of vitamin E are also protective against age-related macular degeneration in humans. Vitamin E is the major antioxidant present in cell membranes; it is highly concentrated in rod photoreceptor outer segments and the retinal pigment epithelium. It may also protect vitamin A from oxidative degeneration the retina.

Proanthocyanidins—Proanthocyanidins are naturally occurring compounds found at high concentrations in fruits, vegetables, wine, tea, nuts, seeds, flowers, bark and cacao. Proanthocyanidins have a wide range of biological activities such as antioxidant and free radical scavenging capabilities, anti-inflammatory and antimicrobial properties, inhibition of cancer cell growth, prevention of low density lipoproteins oxidation, cardioprotection, and inhibition of viral replication. In vitro experiments utilizing grape seed proanthocyanidin extract, GSE, have shown GSE to be a more potent free radical scavenger than vitamin C or vitamin E. Furthermore, GSE has been shown to prevent cataract formation in a hereditary cataractous rat model and in a diabetic rat model. GSE may have use as a dietary supplement to prevent and/or delay cataract formation. GSE significantly decreases TBHP-induced intracellular ROS production and oxidant-induced cell signaling pathways associated with cataractogenesis, as well as UV-induced changes associated with cataractogenesis. It also lowers blood glucose levels in diabetics and improves endothelial cell function.

Zinc—Zinc is an essential trace element essential for numerous homeostatic functions. It is an antioxidant that offers protection against some, but not all, ROS mediated injury. It competitively displaces iron from binding sites on negatively charged phospholipids and prevents its redox cycling. When combined with vitamin E it has synergistic protection against Fe-mediated lipid peroxidation. It is also important to the health of the retina and in the function of vitamin A. Zinc deficiency reduces plasma levels of retinol-binding protein and retinol reductase with a subsequent decrease in vitamin A in the retina. One human study showed it to slow the progression of macular degeneration. Zinc is also important in protecting the lens from cataractogenesis by its antioxidant effects. Zinc deficiency in some species has been associated with increased risk of cataract formation.

Epigallocatechin gallate, EGCG—Both green and black teas significantly inhibit diabetic cataracts by reducing certain biochemical indicators as well as glucose. Another study showed similar results but also suggested an increase in insulin activity. Retard the progression of cataract in selenite induced cataracts in rats. A recent study found that EGCG fed in the water to albino rats attenuated light-induced photoreceptor damage. In addition, EGCG given to rats wherein one eye had an induced increase in intraocular pressure attenuated retinal neuronal death. This supports EGCG's neuroprotective capabilities and may be beneficial in cases of glaucoma.

Alpha Lipoic Acid—Alpha lipoic acid is an antioxidant that potentiates vitamin C and vitamin E levels; it also has anti-inflammatory effects. It has traditionally been used for diabetic neuropathy and in ischemia-reperfusion injury. It was included in this recipe primarily for the numerous diabetic canine patients seen in veterinary practice. It is not in the feline formula as it may not be safe in cats at a dose higher than 30 mg/day.

Alpha lipoic acid is an antioxidant that potentiates Vitamin C and Vitamin E levels. Alpha lipoic acid has anti-inflammatory effects. Alpha lipoic acid has traditionally been used in humans for diabetic neuropathy and in ischemia-reperfusion injury. (Mandelker and Wynn, 2004) Alpha lipoic acid's primary function is to increase the body's production of glutathione, an important antioxidant mechanism in the crystallin lens, that may protect against cataract. One study found that alpha lipoic acid protects the lens from oxidative stress. (Maitra et al., 1995) Alpha lipoic acid is included in Ocu-GLO Rx™ primarily to benefit diabetic canine patients as it promotes normal insulin sensitivity and glucose metabolism. (Jacob et al., 1995, Nichols, 1997) By helping to balance insulin/glucose metabolism, secondary cataract due to hyperglycemia may be slowed or prevented.

JACOB, S., HENRIKSEN, E. J., SCHIEMANN, A. L., SIMON, I., CLANCY, D. E., TRITSCHLER, H. J., JUNG, W. I., AUGUSTIN, H. J. & DIETZE, G. J. (1995) Enhancement of glucose disposal in patients with type 2 diabetes by alpha-lipoic acid. *Arzneimittelforschung*, 45, 872-874.

MAITRA, I., SERBINOVA, E., TRISCHLER, H. & PACKER, L. (1995) Alpha-lipoic acid prevents buthionine sulfoximine-induced cataract formation in newborn rats. *Free Radic Biol Med*, 18, 823-829.

MANDELKER, L. & WYNN, S. (2004) Cellular effects of common nutraceuticals and natural food substances. *Vet Clin Small Anim*, 34, 339-353.

NICHOLS, T. R. J. (1997) Alpha-lipoic acid: Biological effects and clinical implications. *Alternative Medicine Review*, 2, 177-182.

B vitamin mix—The B vitamins function in a variety of essential processes and were included in this recipe for the overall health of the body. Vitamin B1, thiamine, is important in neuromuscular development and maintenance as well as carbohydrate and fat utilization for energy production and cellular metabolism. Vitamin B3, niacin, is likewise involved in energy production but also in fat and steroid synthesis and lowers total levels of serum cholesterol, low density lipoproteins, very low density lipoproteins, and triglycerides. Vitamin B5, pantothenic acid, is essential for breakdown of fatty acids, steroids, cholesterol and amino acids and functions as an antioxidant. It is incorporated into coenzyme A, which is important in oxidative phosphorylation. Vitamin B6, pyridoxine, is essential for hemoglobin formation and important for utilization for stored glucose. It is essential in the metabolism of fats, proteins, and carbohydrates. Vitamin B12, cyanocobalamin, is an enzyme cofactor essential for normal cell growth and red blood cell development. Folic acid, aka vitamin B9, is essential for cell growth and development and for preventing neural tube defects in developing fetuses. It has anticarcinogenic abilities in elderly humans and insufficient intake may result in anemia. Biotin, aka Vitamin H, is an enzyme cofactor involved in biosynthesis of fats and carbohydrates and metabolism of amino acids. Biotin has been shown to improve glucose tolerance and decrease insulin resistance.

Co-Enzyme Q10—Co-enzyme Q10, aka ubiquinol, is a lipid-soluble antioxidant that can be synthesized de novo and regenerated through a specific enzyme system in animal cells. It is not regarded as a vitamin because it is synthesized by all animal tissues. It functions to protect against lipid peroxidation and, therefore, functions as an antioxidant. Ubiquinol mediates electron transport in the mitochondrial respiratory chain, it supports energy metabolism and is a catalyst in ATP production.

SUMMARY OF THE INVENTION

The present invention refers to the use of supplementing an animal or human in effective amounts of a combination of antioxidants for the inhibition or progression of any retinal degeneration, for the prevention or slowing of the progression of cataract formation, for the improvement of dry eye disease, and for the overall enhanced health of the eye. By combining these antioxidants in amounts that are effective and in such a combination that various antioxidant pathways are addressed, this will optimize the ocular health of normal individuals and enhance conditions that are exacerbated or caused by oxidative stress.

DETAILED DESCRIPTION OF THE PREFERRED EMBODIMENTS

The present invention refers to the use of supplementing an animal or human in effective amounts of a combination of antioxidants for the inhibition or progression of any retinal degeneration, for the prevention or slowing of the progression of cataract formation, for the improvement of dry eye disease, and for the overall enhanced health of the eye. By combining these antioxidants in amounts that are effective and in such a combination that various antioxidant pathways are addressed, this will optimize the ocular health of normal individuals and enhance conditions that are exacerbated or caused by oxidative stress.

The supplement may be any suitable form of a pill, capsule preferably but not limited to a soft chewable gelatin capsule, tablet, chewable treat, liquid, slurry, or any other ingestible form, containing the previously mentioned ingredients in the effective ranges to be specified here. Not only is the specific combination of synergistic ingredients essential to the effectiveness of said invention, but the proper dosing as well. It is believed that sub-therapeutic levels are currently being proposed and commercially provided, contrary to successful studies showing a need for higher dosage levels. It is vital and unique to this invention that proposed ingredients be present in sufficiently high concentrations and purity, a minimum of 90 percent purity must be maintained, but preferably 95-99.9 percent purity for all ingredients, in order to maximize the potential for halting or delay of the previously discussed ocular diseases.

Example 1

Production of a chewable, flavored soft gelatin capsule is accomplished by filling soft gelatin capsules with the active ingredients which have been combined into a thick oil suspension, or slurry, and flavored with a suitable flavoring agent. The capsules are filled under specific laboratory conditions, utilizing liquid nitrogen to displace any air from remaining inside the filled capsules. The capsule is then sealed and allowed to dry. A powdered flavoring may be dusted over the finished capsule, or a light spraying of a misted form of the flavoring may be passed over the product, to enhance appeal and compliance of the product. The process of filling the capsules under liquid nitrogen controlled conditions limits, or eliminates, air from being trapped inside the capsule, therefore limiting, or nearly eliminating, the oxidation process known to destroy anti-oxidants.

Example 2

Production of a soft chewable flavored dosage form, or treat, is accomplished by combining active ingredients with inert fillers such as but not limited to soy protein, flour, xanthan gum, and silica, with flavorings of sugar, appropriate levels of liquid flavorings, and commercial dog food added to increase palatability. The product is then pressed into 5 gram chewable doses and allowed to dry.

Example 3

An opaque gelatin capsule may be filled with 1 ml active ingredients, omitting the flavoring agents. Capsules are then tightly sealed and provided as an oral dosage. Note: Example 1 is the preferable system for capsules, even is the absence of flavoring inside or out, as the integrity of the product produced under the liquid nitrogen process is preferable.

| Ingredient | Amount per kg body weight, based on 1 gelcap per day |
|---|---|
| Lutein and zeaxanthin | 1.13 to 3 mg |
| Omega fatty acids | 18.8 to 51.2 mg |
| Vitamin C | 7.5 to 20.8 mg |
| Vitamin E | 3.75 to 10.4 mg |
| GSE | 1.9 to 5.2 mg |
| zinc | 0.38 to 1.04 mg |
| Lycopene | 0.1 to 0.3 mg |
| EGCG | 1.13 to 3.125 mg |
| alpha lipoid acid | 1.9 to 5.2 mg |
| B1, thiamine | 0.0075 to 0.02 mg |
| B3, niacin | 0.09 to 0.25 mg |
| B5, pantothenic acid | 0.075 to 0.2 |
| B6, pyridoxine HCl | 0.0075 to 0.02 mg |
| B12, cyanocobalamin | 0.0002 to 0.0005 mg |
| Folic acid | 0.0015 to 0.004 mg |
| Biotin | 0.00075 to 0.048 mg |
| Co Q10 | 1.9 to 5.2 mg |
| Silymarin | 7 to 15 mg |

The present invention is a combination of nutritional supplements that may enhance overall ocular health, specifically slow/prevent retinal degenerative diseases and cataracts.

The polyphenol, grapeseed extract, free radical scavenger chelation of transition metals, protects against lipid peroxidation of LDL cholesterol; inhibits against DNA fragmentation, apoptosis; protects retinal microvasculature possibly by increasing the rate of rhodopsin regeneration; has a Vitamin E sparing effect; inhibits formation of proinflammatory cytokines IL1β and TNF. It may also lower blood glucose levels in diabetic patients and improve endothelial cell function.

The carotenoid pigments including lutein and zeaxanthin act as antioxidants and protect cell membranes by stabilizing the oxygen radicals produced when phagocytic granulocytes undergo respiratory bursts that destroy intracellular pathogens.

The carotenoid, lycopene, prevents free radical damage by reactive oxygen species; modulates intercellular gap junction communication; and may protect against hyperglycemia.

The omega fatty acids are potent antioxidants that slow the progression or prevent the onset of various forms of retinal degeneration.

The carotenoid, lycopene, prevents free radical damage by reactive oxygen species; modulates intercellular gap junction communication; and may protect against hyperglycemia.

Vitamin C, ascorbic acid, is normally present in the aqueous humor and lens of most species and elevated levels protect against some types of cataract.

Vitamin E, alone or mixed tocopherols and tocotrienols, inhibits COX2 activity; is the major antioxidant present in cell membranes; and is concentrated in rod photoreceptor outer segments and the retinal pigment epithelium. It may also protect vitamin A from oxidative degeneration in the retina. Therefore, it may protect against various forms of retinal degeneration.

The polyphenol, grapeseed extract, free radical scavenger chelation of transition metals, protects against lipid peroxidation of LDL cholesterol; inhibits against DNA fragmentation, apoptosis; protects retinal microvasculature possibly by increasing the rate of rhodopsin regeneration; has a Vitamin E sparing effect; inhibits formation of proinflammatory cytokines IL1β and TNF. It may also lower blood glucose levels in diabetic patients and improve endothelial cell function.

Zinc offers protection against some, but not all, ROS mediated injury; competitively displaces iron from binding sites on negatively charged phospholipids; and prevents its redox cycling.

EGCG quenches reactive oxygen species, prevents oxidative cross-linking of test proteins, and inhibits single strand DNA breaks in whole cells. It also counteracts the oxidative insult from cigarette smoke and retards the progression of cataract in selenite induced cataracts in rats. It also inhibits diabetic cataracts in rat models by a hypoglycemic effect and also decreased triglycerides in the same rats.

The B vitamins function in a variety of essential processes and were included in this recipe for the overall health of the body including neuromuscular development and maintenance as well as carbohydrate and fat utilization—Vitamin B1, thiamine; energy production, fat and steroid synthesis and lowering of total levels of serum cholesterol, low density lipoproteins, very low density lipoproteins, and triglycerides—Vitamin B3, niacin; breakdown of fatty acids, steroids, cholesterol and amino acids and functions as an antioxidant—Vitamin B5, pantothenic acid; hemoglobin formation and utilization of stored glucose as well as metabolism of fats, proteins, and carbohydrates—Vitamin B6, pyridoxine; as an enzyme cofactor essential for normal cell growth and red blood cell development—Vitamin B12, cyanocobalamin; and biosynthesis of fats and carbohydrates and metabolism of amino acids as well as improved glucose tolerance and decreased insulin resistance.

Folic acid, i.e. vitamin B9, may have anticarcinogenic abilities in the elderly

Alpha lipoic acid, an antioxidant, improves glucose transport in muscles following exercise and is used in the management of insulin resistance i.e. type II diabetes.

Biotin, i.e. Vitamin H, is an enzyme cofactor involved in biosynthesis of fats and carbohydrates and metabolism of amino acids. Biotin has been shown to improve glucose tolerance and decrease insulin resistance which is important in the prevention and control of diabetes.

Co-enzyme Q10, an antioxidant, supports energy metabolism and is a catalyst of ATP production.

Milk thistle, also referred to as silymarin, silibinin, Silybum marianum, mariendistel, and Carduus marianus is a potent antioxidant with relevant effects against biological reactive oxygen species and lipid peroxidation. Silymarin also protects skin cells against ultraviolet radiation A induced damage including DNA strand breaks, lipid peroxidation and oxidative stress.

The present invention is a nutritional supplement system for enhancing the overall ocular health of animals by slowing and preventing degenerative diseases, cataracts and other maladies. The system comprises components in combination. In its broadest embodiment, the first component is provided is 1.13 to 3 mg lutein and zeaxanthin. The next component provided is 18.8 to 51.2 mg omega fatty acids. The last component provided is 1.9 to 5.2 mg grape seed extract. The weight of the components of the system are based upon an amount per kg body weight based on 1 dose per day.

An additional embodiment the system adds a nutritional supplement for abating heart disease. The supplement for abating heart disease is chosen from the class of heart disease abating supplements including 3.75 to 10.4 mg vitamin E and 1.9 to 5.2 mg Co Q10.

In another embodiment, the system adds an additional nutritional supplement for abating cataracts. The supplement for abating cataracts is chosen from the class of cataract abating supplements including 7.5 to 20.8 mg vitamin C and 0.1 to 0.3 mg lycopene.

In still another embodiment, the system adds an additional nutritional supplement for abating cancer. The supplement for abating cancer is chosen from the class of cancer abating supplements including 0.38 to 1.04 mg zinc, 1.13 to 3.125 mg EGCG, green tea, 0.0015 to 0.004 mg folic acid, and 7 to 15 mg silymarin.

In yet another embodiment, the system adds an additional nutritional supplement for abating diabetes. The supplement for abating diabetes is chosen from the class of diabetes abating supplements including 1.9 to 5.2 mg alpha lipoid acid and 0.00075 to 0.048 mg biotin.

In a final embodiment, the system adds an additional nutritional vitamin supplement for overall health enhancement. The supplement for overall health enhancement is chosen from the class of health enhancing vitamin supplements including 0.0075 to 0.02 mg B1, thiamine; 0.09 to 0.25 mg B3, niacin; 0.075 to 0.2 mg B5, pantothenic acid; 0.0075 to 0.02 B6, pyridoxine Hcl; and 0.0002 to 0.0005 mg B12, cyanocobalamin.

Lastly the present invention is a method for enhancing overall ocular health in animal patients. The method comprises a a plurality of steps.

The first step is providing a nutraceutical. The nutraceutical includes, in combination, 1.13 to 3 mg lutein and 18.8 to 51.2 mg omega fatty acids and 1.9 to 5.2 mg grape seed extract and 1.9 to 5.2 mg alpha lipoic acid.

The next step is determining the weight of each dose of the components in the combination based upon an amount per kg body weight of the animal patients.

The last step is administering 1 dose of nutraceutical per day to animals suffering from ocular health issues including any degenerative retinal disease and diabetic cataracts. The administering being prior to and following cataract surgery for the diminishment and prevention of secondary cataracts.

It should be appreciated that the components of the present invention have primary benefits as set forth above. It should be further appreciated that such components also have an additional benefit and/or benefits, known or not known. Together, however, the components of the present invention entice ocular and additional benefits, particularly in animals.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A method for enhancing ocular health in a non-human subject comprising the steps of:
   (a) determining the body weight of the subject in kilograms;
   (b) administering 1 dose per day of a nutraceutical to the subject in need thereof, wherein the dose of the nutraceutical consists of 1.3 to 3 mg/kg BW lutein, 18.8 to 51.2 mg/kg BW omega fatty acids, 1.9 to 5.2 mg//kg BW grapeseed extract, and 1.9 to 5.2 mg/kg BW alpha lipoic acid.

2. The method of claim 1, wherein said subject suffers from a degenerative retinal disease or diabetic cataracts.

3. The method of claim 1, wherein said administering is performed prior to and following cataract surgery to diminish the development of secondary cataracts.

* * * * *